(12) United States Patent
Babson

(10) Patent No.: US 7,670,553 B2
(45) Date of Patent: Mar. 2, 2010

(54) CAROUSEL SYSTEM FOR AUTOMATED CHEMICAL OR BIOLOGICAL ANALYZERS EMPLOYING LINEAR RACKS

(75) Inventor: Arthur L. Babson, Chester, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 617 days.

(21) Appl. No.: 11/087,809

(22) Filed: Mar. 24, 2005

(65) Prior Publication Data

US 2006/0245865 A1 Nov. 2, 2006

(51) Int. Cl.
*G01N 35/02* (2006.01)
(52) U.S. Cl. .............................. 422/64; 422/65; 436/47
(58) Field of Classification Search ................................
414/331.02–331.03, 331.05; 198/346.2,
198/347.3, 463.1; 436/47–48; 422/64–65
See application file for complete search history.

(56) References Cited

U.S. PATENT DOCUMENTS

| 3,785,773 | A | * | 1/1974 | Rohrbaugh | 422/102 |
|---|---|---|---|---|---|
| 3,832,135 | A | * | 8/1974 | Drozdowski et al. | 436/47 |
| 4,639,242 | A | | 1/1987 | Babson | |
| 4,678,752 | A | * | 7/1987 | Thorne et al. | 435/287.3 |
| 4,849,177 | A | * | 7/1989 | Jordan | 422/64 |
| 4,863,693 | A | * | 9/1989 | Howell | 422/64 |
| 4,956,148 | A | * | 9/1990 | Grandone | 422/64 |
| 4,970,053 | A | * | 11/1990 | Fechtner | 422/102 |
| 5,008,082 | A | | 4/1991 | Shaw | |
| 5,035,861 | A | * | 7/1991 | Grandone | 422/64 |
| 5,075,082 | A | * | 12/1991 | Fechtner | 422/102 |
| 5,084,240 | A | | 1/1992 | Babson | |
| 5,098,845 | A | | 3/1992 | Babson | |
| 5,128,103 | A | * | 7/1992 | Wang et al. | 422/64 |
| 5,141,871 | A | * | 8/1992 | Kureshy et al. | 436/47 |
| 5,147,529 | A | * | 9/1992 | Lee et al. | 210/695 |
| 5,167,922 | A | * | 12/1992 | Long | 422/58 |
| 5,192,506 | A | * | 3/1993 | Kureshy et al. | 422/64 |
| 5,207,987 | A | * | 5/1993 | Kureshy et al. | 422/67 |
| 5,219,526 | A | * | 6/1993 | Long | 422/64 |
| 5,240,678 | A | * | 8/1993 | Litsche | 422/64 |
| 5,258,309 | A | | 11/1993 | Babson et al. | |
| 5,316,726 | A | | 5/1994 | Babson et al. | |
| 5,318,748 | A | | 6/1994 | Babson et al. | |
| 5,320,808 | A | * | 6/1994 | Holen et al. | 422/64 |
| 5,320,809 | A | * | 6/1994 | Dunn et al. | 422/64 |
| 5,324,481 | A | * | 6/1994 | Dunn et al. | 422/64 |
| 5,358,691 | A | * | 10/1994 | Clark et al. | 422/64 |
| 5,380,488 | A | | 1/1995 | Wakatake | |
| 5,620,898 | A | | 4/1997 | Yaremko et al. | |
| 5,627,522 | A | | 5/1997 | Walker et al. | |

(Continued)

FOREIGN PATENT DOCUMENTS

EP 290018 A2 * 11/1988

(Continued)

*Primary Examiner*—James Keenan

(57) ABSTRACT

An automated chemical or biological sample analyzer includes a plurality of linear sample carrying racks that are moved to a processing station for conducting an analysis using one or more carousel devices. Under computer control, rotational movements of the carousel or carousels, linear movements of the transfer or shuttle mechanisms, and operation of a pipetting station are performed in a coordinated fashion so as to handle the processing of a large number of samples simultaneously in an optimized fashion that allows random ordering of samples for processing.

34 Claims, 8 Drawing Sheets

U.S. PATENT DOCUMENTS

| | | | |
|---|---|---|---|
| 5,632,399 A | 5/1997 | Palmieri et al. | |
| 5,646,049 A * | 7/1997 | Tayi | 436/518 |
| 5,721,141 A | 2/1998 | Babson et al. | |
| 5,723,092 A | 3/1998 | Babson | |
| 5,776,784 A * | 7/1998 | Kegelman et al. | 436/526 |
| 5,807,523 A | 9/1998 | Watts et al. | |
| 5,885,529 A | 3/1999 | Babson et al. | |
| 5,885,530 A * | 3/1999 | Babson et al. | 422/65 |
| 5,902,548 A * | 5/1999 | Watts et al. | 422/63 |
| 5,902,549 A | 5/1999 | Mimura et al. | |
| 6,027,691 A * | 2/2000 | Watts et al. | 422/64 |
| 6,074,617 A * | 6/2000 | DeYoung et al. | 422/104 |
| 6,358,472 B1 * | 3/2002 | DeYoung et al. | 422/65 |
| 6,723,288 B2 * | 4/2004 | Devlin et al. | 422/65 |
| 6,943,030 B2 * | 9/2005 | Gebrian et al. | 436/55 |
| 7,029,922 B2 * | 4/2006 | Miller | 436/180 |
| 7,107,936 B2 * | 9/2006 | Fantin et al. | 119/655 |
| 7,112,303 B2 * | 9/2006 | Itoh | 422/72 |
| 7,169,356 B2 * | 1/2007 | Gebrian et al. | 422/64 |
| 7,175,334 B2 * | 2/2007 | Babson et al. | 366/109 |
| 7,185,288 B2 * | 2/2007 | McKeever | 715/792 |
| 7,390,458 B2 * | 6/2008 | Burow et al. | 422/63 |
| 7,507,377 B2 * | 3/2009 | Rousseau et al. | 422/102 |
| 2003/0054542 A1 | 3/2003 | Burns et al. | |
| 2005/0013736 A1 * | 1/2005 | McKeever | 422/63 |
| 2005/0106747 A1 * | 5/2005 | Chaoui et al. | 436/165 |
| 2005/0159982 A1 * | 7/2005 | Showalter et al. | 705/2 |

FOREIGN PATENT DOCUMENTS

| | | | |
|---|---|---|---|
| EP | 325101 A1 * | 7/1989 | |
| JP | 01189561 A * | 7/1989 | |
| JP | 01212362 A * | 8/1989 | |
| JP | 01219564 A * | 9/1989 | |
| JP | 01229975 A * | 9/1989 | |
| JP | 01250759 A * | 10/1989 | |

* cited by examiner

Figure 4a                    Figure 4b

CAROUSEL SYSTEM FOR AUTOMATED CHEMICAL OR BIOLOGICAL ANALYZERS EMPLOYING LINEAR RACKS

FIELD OF THE INVENTION

The present invention generally relates to automated chemical analyzers, such as, for example, automated immunoassay analyzers, and more particularly, to a carousel system which handles linear racks, each of which hold a plurality of samples or controls. The invention thus combines the immediate access to samples benefits of a carousel system with the benefit of enhanced automation by sequential presentation offered linear rack based systems.

BACKGROUND DESCRIPTION

Automating chemical analyses is a desirable objective in a number of situations. For example, in the clinic or hospital setting, a large number of patient blood or urine samples need to be analyzed on a daily basis for a wide variety of different antigens or analytes. Highly advanced systems have been developed for analyzing these types of samples, and for allowing different tests to be performed on different samples as well as for recording test results for subsequent use in, for example, patient assessment and care. Exemplary systems are described in U.S. Pat. Nos. 6,027,691; 5,902,548; 5,885,530; 5,885,529; 5,807,523; 5,723,092; 5,721,141; 5,632,399; 5,620,898; 5,318,748; 5,316,726; 5,258,309; 5,098,845; 5,084,240; 5,008,082 and 4,639,242 all of which are herein incorporated by reference. As another example, automated systems may be used for detecting contaminants in water sources, food products, etc.

Despite the advanced systems for automated chemical analysis, there remains a need for improving the level of automation, the mechanisms which allow random access to and testing of samples, and the speed in processing large numbers of samples (i.e., throughput). Presently, the current automated technologies either involve carousels, which allow large numbers of samples or agents to be present and easily accessible, or linear racks and conveyers where the materials stored in the racks are easily presented for operations in a sequential manner. While the carousel systems have the advantage of easy access to large numbers of samples, the prior art systems suffer from having to empty the carousels in a batch like process in order to handle new samples. Conversely, while the linear rack based systems allow for easy automation, it is generally more difficult to retrieve a sample at different times to perform different tests.

SUMMARY OF THE INVENTION

It is therefore an object of this invention to combine the benefits of carousel systems and linear rack systems, while avoiding the disadvantages of both.

According to the invention, an improved sample handling system, which may be incorporated into automated chemical or biological (e.g., immunoassay) analyzers, includes one or more carousels with radially distributed slots, each of which can accommodate a linear rack containing a plurality of samples or controls distributed along the length of the linear rack. The linear racks preferably include receptacles for holding containers (e.g., test tubes) filled with samples or controls, and, more preferably, the containers can be of varying sizes. Preferably, the test tubes are labeled with a bar code or an RFID tag identifying the contents of the tube, and the linear racks are also labeled with a bar code or RFID tag. In a preferred configuration using bar coding, the bar codes on the test tubes and on the linear racks can be read at the same time using the same bar code reader. In operation, a computer controller will track information related to the location of linear racks and test tubes, and by associating bar code or RFID identity information of the rack and bar code or RFID identity information of the test tubes, the controller can easily manage retrieval, transfer, and pipetting operations of samples which need to be accessed a number of different times (e.g., for performing different tests on the same sample). Bar code labels may be permanently imprinted on linear racks or labels may be printed and applied to linear racks as well as to test tubes. Similarly, RFID tags might be affixed to and removable from both linear racks and test tubes.

Mechanical transfer devices, operated under computer control, engage the linear racks and transfer them, for example, from a rack loader into a carousel, between two adjacent carousels, and between a carousel and a separate control storage compartment. This may preferably be accomplished using a belt or chain drive which moves a transfer slide with a transfer pin mounted thereon, where the transfer pin engages a slot located, for example, in the bottom of the linear rack. A motor, operating under computer control, will cause the transfer pin to engage the slot in the linear rack and move the linear rack, for example, into a slot in the carousel. When in the carousel, the linear rack will be retained by, for example, a flat spring and button connection that fits within a depression in the bottom of the linear rack. By advancing the carousel slightly, the transfer pin can be moved out of the linear rack and to a position outside the circumference of the carousel through a channel formed in the bottom of the carousel. Preferably, a spring or other elastic device is used to hold the linear rack firmly in place against a side wall of the slot in the carousel.

Carousels offer the flexibility of random access to all samples, and immediate access to any sample. Once in the carousel, samples on the linear rack can be processed, for example, movement to a pipetting station or diluting station, movement to a second or third carousel, etc. Ideally, the length of time between loading the linear rack onto the carousel and the further processing will be handled under computer control which will consider the other samples on board the one or more carousels of the automated chemical or biological analyzer, the tests being conducted for each of the samples, as well as other factors such as rush or "STAT" tests to be conducted on a priority basis.

Movements of the one or more carousels, the mechanical transfer devices, pipetters and other components in the chemical and biological analyzer are preferably accomplished under computer control so as to minimize or eliminate involvement of technicians. This is accomplished by tracking the linear rack that is labeled with a bar code, RFID tag, or other device, tracking the positions of the linear racks in the carousel or carousels as well as the testing to be performed on the samples in the linear racks, and coordinating the movements of the transfer devices and pipetters.

The capacity of the automated chemical or biological analyzer can be made quite large by using multiple carousels in a series with transfer devices positioned to move linear racks between the carousels, as well as by using linear racks that can accommodate larger numbers of samples. In a preferred embodiment, the linear racks may hold five sample tubes, and the carousels may have twenty slots. Thus, an automated chemical or biological analyzer equipped with two carousels configured in the preferred embodiment may be processing up to two hundred samples at a time. After testing of the samples, the linear rack can be selectively removed from the carousel using the mechanical transfer device, and may be deposited in a rack loader or suitable storage area.

In one embodiment of the invention, controls are loaded into the carousel system on a linear rack in the same fashion as samples to be tested. These controls can be selectively stored in a slot on the carousel, or, more preferably, be stored in a storage area separate from a carousel. Transfers from the carousel to the storage area will be accomplished with a mechanical transfer device operating under computer control in the same fashion as discussed above. The controls can be selectively retrieved (e.g., transferred back onto the carousel followed by the carousel being rotated to pipetting position), for periodic calibration or testing of the automated chemical or biological analyzer, and then re-loaded into the storage compartment. In this embodiment, the user is not required to load controls by a separate operation (i.e., controls can be automatically loaded into the machine from the rack loader used for transporting linear racks of samples), and the controls can be periodically used multiple times without interrupting the operations of the chemical or biological analyzer.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1:
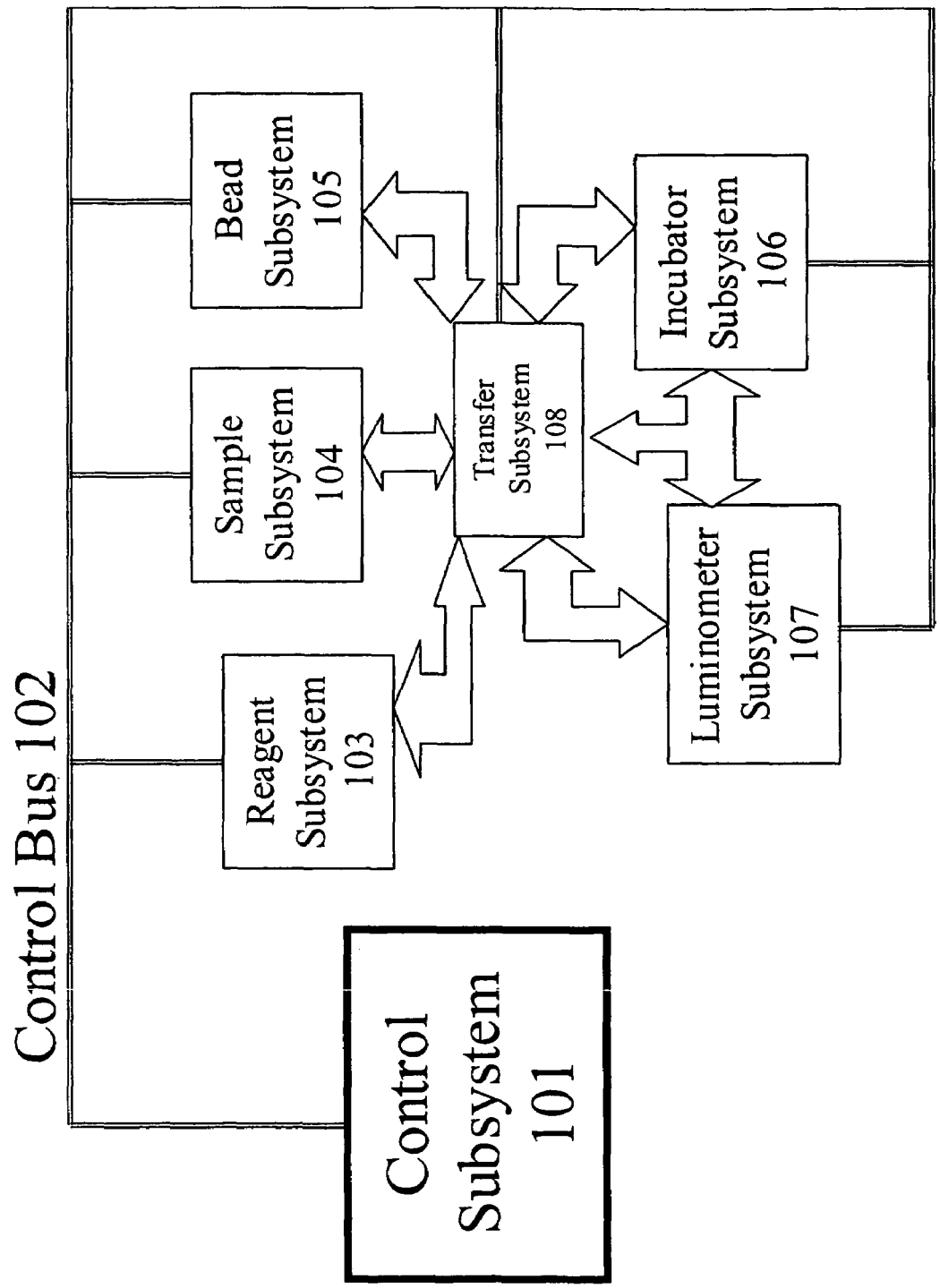
FIG. 1 is an overview of an automated immunoassay analyzer according to the preferred embodiments of the invention.

For illustrative purposes only, FIG. 1 shows the subsystems for performing operations in an automated immunoassay analyzer; however, it should be understood that this invention can be practiced with chemical analyzers per se, and is not limited to use in automated immunoassay analyzers. Automated immunoassay analyzers are complex systems designed to process large numbers of patient samples obtained at a clinic or hospital with minimal involvement of a technician. It should be understood that this invention provides for sample handling in a highly automated and flexible manner, and may be amenable for use in a variety of existing automated chemical or immunoassay analyzers or could be incorporated in the future into newer automated chemical or immunoassay analyzers.

At its core, the control system 101 manages and coordinates the operations of all of the subsystems by sending commands and by receiving signals from the subsystems via the control bus 102. In operation of an automated immunoassay analyzer, samples of biological material (e.g., blood, urine, plasma, etc.) are placed in the sample subsystem 104. This can be accomplished manually, or by retrieving samples (and, most preferably in the preferred embodiment of this invention, linear racks containing samples) from a rack loader which has been loaded with samples obtained throughout, for example, a hospital or clinic. The samples within the sample subsystem 104 can be diluted prior to making measurements or can be tested in their undiluted state depending on direction from the control subsystem 101. Preferably, a bead subsystem 105 adds an appropriate substrate having a bound "analyte binding compound" to a test vessel in which, for example, an antibody-antigen binding interaction will be performed for testing for the amount of an antibody or antigen of interest in the sample. A large number of different analytes can be tested using beads or other substrates that are added to a test vessel. In addition, multiple tests for different analytes in the same sample can be performed simply by adding the appropriate bead with bound analyte to each of several test vessels, and then adding sample from the sample tubes on the linear racks to each of the test vessels (i.e., immunoassay or chemical analyzers which include bead subsystems 105 provide for significant flexibility in processing samples for test). The reagent subsystem 103 is used for adding reagents to test vessels under control of the control subsystem 101. Similarly, the incubator subsystem 106 incubates test vessels, preferably with vessel agitation, for predetermined periods of time prior to testing, and the luminometer subsystem 107 performs measurements on samples which have been combined with reagents and beads, and which have been incubated and washed (it being understood that some analyzers may utilize phosphorescence, fluorescence, or colorimetric changes instead of chemiluminescence (the preferred indicator in the immunoassay embodiment of this invention)).

Movement between stations is accomplished using the transfer subsystem 108. The control subsystem 101 coordinates the operations being performed within subsystems 102, 103, 104, 105, 106, and 107, and the transfers being performed by transfer subsystem 108, and preferably considers the tests being performed on all of the samples which have been loaded, thereby optimizing the order in which certain tests are performed. In addition, the control subsystem 101 preferably accommodates rush or "STAT" tests such that certain tests on certain samples can be performed preferentially to other tests on other samples present in the automated chemical or biological analyzer.

Preferably, the subsystems 103, 104, 105, 106, and 107, take advantage of identification technologies such as, for example, bar coding and RFIDs. That is, reagents loaded on a reagent subsystem 103 would be identified for the control subsystem 101, so that the position of a particular reagent would be known and managed by the control subsystem 101. Similarly, beads to be added to test vessels using the bead subsystem 105, would be added using bar coded or RFID tagged bead dispensers (not shown), such that the control subsystem 101 would be made aware of the location of the beads to be dispensed. Notification for replenishment of the reagents or beads may be accomplished using sensors at the reagent subsystem 103 and the bead subsystem 105 which communicate information to the control subsystem 101 through the control bus 102. As will be discussed in more detail below, the sample subsystem 104 will utilize bar codes or RFID tags or other identification schemes to notify the control subsystem 101 of the location of a sample within the automated chemical or biological analyzer. By tracking the location of a linear rack and by having the identifying information of the test tubes associated with particular linear racks, the controller can accommodate random and immediate access to any sample in any rack in any carousel.

This invention is directed to the sample subsystem 104. The sample subsystem 104 can be employed in a wide variety of automated immunoassay analyzers, and should be applicable to any analyzer which requires access to multiple test samples for diagnostic purposes.

Figure 2:
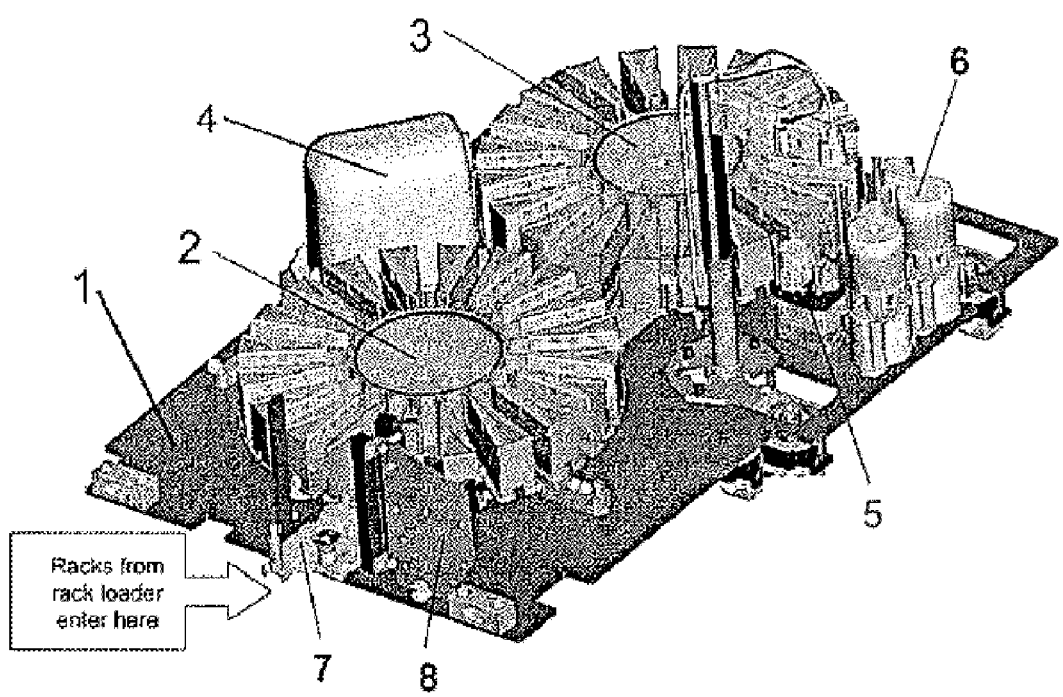
FIG. 2 is an illustration of the major elements of the carousel system.

FIG. 2 shows a more detailed view of a preferred embodiment of a carousel system according to the present invention which is used in the sample subsystem 104. FIG. 2 shows a platform 1 on which is located two carousels 2 and 3, a control storage element 4, a pipetting station 5 (preferably, a similar pipetting station is positioned on the end of the platform adjacent carousel 3 and dilution station 6 so that two pipetters can be used to simultaneously pipette samples from two different sample tubes), a dilution station 6, a plurality of transfer mechanisms 7 (the transfer mechanism between the loader and carousel being shown, and similar transfer mechanisms being present between carousels 2 and 3, and between carousel 3 and control storage element 4), and sample identification system 8. It should be understood that the number of carousels can vary within the practice of the invention, and the practice of this invention contemplates its application to a single carousel, two carousels, or three or more carousels. The advantage of having several carousels, is that a large number of samples can be handled at any one time. Further, there is more flexibility in machine design and operation in using several smaller carousels as opposed to a single larger carousel. The location of the control storage element 4, pipetting station 5, and diluting station 6 will vary depending on the number of carousels employed in the sample subsystem 104.

While FIG. 2 shows a single transfer mechanism 7 which obtains linear racks from a rack loader (not shown), it should be understood that an identical or similar transfer mechanism will be positioned so as to move linear racks between carousels 2 and 3, and between carousel 3 and control storage element 4. Thus, a sample in a linear rack that is loaded into a slot of carousel 2 can remain in carousel 2 for a period of time determined by the tests to be performed in the linear rack, the tests to be performed in all of the other linear racks loaded into carousels 2 and 3, and any priorities which have been set by a technician to perform some tests more quickly than others. In operation, carousels 2 and 3 are preferably rotatable both in the clockwise and counterclockwise directions under computer control. Linear racks on carousels 2 and 3 can travel around the full 360 degree rotation of either carousel any number of times before samples are retrieved by the pipetter 5.

In the embodiment shown in FIG. 2, a linear rack is rotated half a rotation of the carousel from the site of rack loading to the site of transfer from one carousel 2 to the other carousel 3 (best shown as the two aligned slots in carousels 2 and 3 at their closest point points to each other). In carousel 3, the linear rack is then rotated to one or more positions which are accessible by one or more pipetters 5 for obtaining sample and transferring the sample to a test vessel. If required, dilutions can be performed at station 6. It should be understood that other pipetting systems in addition to the pipetting station 5 shown in FIG. 2 can be added and used in combination in the sample subsystem, and that pipetting can be used to retrieve sample from the linear rack for transferring to a test vessel (not shown) used in, for example, an immunoassay analyzer. In operation of the embodiment of FIG. 2, samples can remain on carousel 3 or be transferred back to carousel 2 and remain on carousel 2 until all tests on the samples in the rack are completed. Depending on the configuration of the pipetting systems 5 and dilution stations 6, the carousel system might allow for retrieval of a sample from either carousel or from more than one position on a single carousel. Once all tests have been initiated on all of the samples on a linear rack, the linear rack can be ejected back to the rack loader for storage.

The control storage element 4 preferably provides an onboard storage space in the automated chemical or biological sample analyzer for control samples which may be used to calibrate the analyzer prior to the performance of certain tests and/or periodically during operation of the analyzer. The control storage element 4 preferably houses the control samples in a preferred storage environment which assures stability. For example, in most applications the environment will be designed to assure low evaporation rates for the control (e.g., low (e.g. refrigerator) temperatures, and possibly higher humidity). Furthermore, the control storage element 4 preferably has a housing which protects the control samples from exposure to dust or other contaminants, as well as any damaging radiant energy (e.g., light or uv light) during extended operation of the analyzer.

Preferably, the control samples are added to the analyzer in the same manner as samples to be tested. That is, they are loaded onto a linear rack which will be either transferred automatically from a rack loader using transfer mechanism 7 into the first carousel 2 or will be manually placed on the transfer mechanism 7 for insertion into the first carousel. Thereafter, under computer control, the linear rack containing the control samples will be passed to the second carousel 3 and then will be passed into the control storage element 4. Preferably, the control storage element 4 will house at least two linear storage racks filled with control samples. When needed, a transfer mechanism will transfer the linear rack with control samples back into the second carousel 3, which will then transport the linear rack to the pipetting station 5. The control sample can then be either diluted at the diluting station 6, or pipetted directly into a test vessel (not shown), which preferably passes along, under computer control, outside of platform 1. Then, the linear rack with control sample will be moved back into the control storage element 4 using movements of carousel 3 and the transfe mechanism located between the carousel 3 and control storage element 4. The configuration thus has the advantage that the operator is not required to periodically load control samples (they are stored on board). The configuration also has the advantage of simplicity because the operator does not need any special mechanism to load the controls (i.e., they are loaded in the same manner as samples to be tested). However, it should be understood that in some applications, it may not be desirable to have control samples on board, and in these applications the control storage element 4 might simply be eliminated (in which case, the linear rack with the control samples would simply occupy a slot within one of the carousels).

FIG. 2 also shows an identification station 8 located adjacent to a transfer mechanism 7. In the configuration shown in FIG. 2, the identification can read bar codes, RFID tags, or other identifying markings on linear racks and sample tubes as they are loaded into carousel 2 from the rack loader using the transfer mechanism 7. The identification information on the linear rack and sample tubes will be relayed from the identification station 8 to the control system 101, and by tracking the slot in carousel 2 in which the particular linear rack and sample tubes identified at identification station 8 is loaded, as well as the movements of the carousels 2 and 3 (if more than one carousel is employed), the control system 101 will be able to better control how and when a linear rack having particular samples thereon is presented to the pipetting station 5 for, for example, transferring sample to a test vessel to perform an immunoassay. The identifying information determined at identification station 8 can thus be used to allow both random and immediate access to any sample stored in any rack in any slot in any carousel of the inventive system. As noted previously, the controller preferably considers all samples on board the carousels for determining an optimized order for tests, as well as the priorities of any rush tests to be performed.

Figure 3:
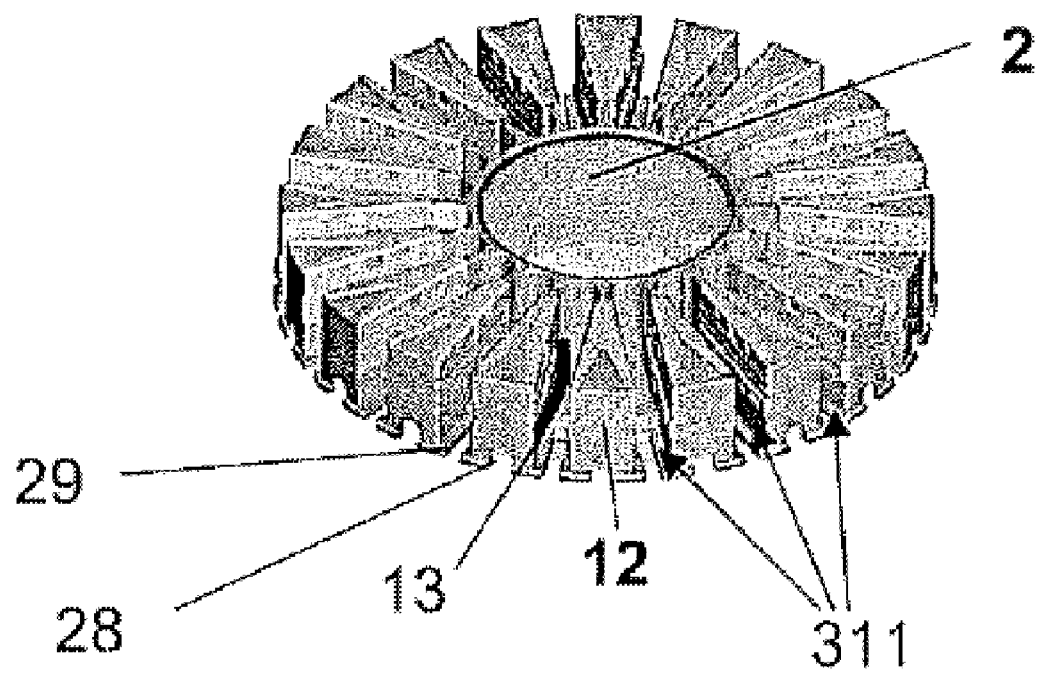
FIG. 3 is an illustration of the sample carousel.

FIG. 3 shows carousel 2 has a number of slots 11 separated by wedge regions 12. Due to the shape of wedge regions 12, the slots 11 are linear and extend along a radius of the carousel. The center section of each slot 11 has a guide slot 29 in which a component of the transfer mechanism, which will be discussed in more detail below, will be able to move freely when transporting a linear rack into the slot 11. Furthermore, the guide slot 29 extends into the adjacent wedge region 12, and the wedge region 12 has a groove 28 at its base so as to allow the component of the transfer mechanism to be withdrawn from the carousel 2 after a linear rack is installed. These grooves 28 and guide slots 29 are also used when the transfer mechanism retrieves a linear rack from the slot 11 of the carousel 2.

To assist in holding the linear rack firmly in position, each slot preferably includes an elastic spring member 13 which forces the linear rack against one of the side walls of the slot 11. Having the linear rack forced against a side wall of a slot may provide certain advantages in being able to more easily align the pipetter of pipetting station 5. Thus, in some applications, it may be preferable to have the elastic spring member 13 located on the same side of each slot in a carousel 2. Further, in some applications which will involve a transfer of a linear rack carrying test samples or control samples, it may be advantageous to have the spring members of adjacent carousels located on the opposite walls of the slots 11. As will be explained in more detail below in connection with FIGS. 4a and 4b, when using a linear rack with openings on one side and a closed back member, it will be advantageous to have the springs 13 on one carousel on one side wall of slots 11 while the springs 13 on the other carousel are on the opposite side wall of slots 11, such that the springs 13 in each carousel always contact the closed back member of the linear rack.

While FIG. 3 shows twenty slots in the carousel 2, it should be understood that the number of slots can vary depending on the design and needs of the analyzer. Further, while FIG. 2 shows two carousels 2 and 3 of the same size with the same number of slots 11, it should be clear that size of the carousels could vary with respect to each other, as well as the number of slots 11; however, in any system requiring transfers between two adjacent carousels 2 and 3, the analyzer will preferably be constructed such that the slots of adjacent carousels are aligned in order to effect a simple, linear transfer from one carousel to the other.

As noted above, the carousels 2 and 3 preferably are each rotatable 360° in either the clockwise or counterclockwise direction, and movements are controlled by a computer in a coordinated fashion so as to allow alignment with a transfer mechanism to permit loading or retrieval of a linear rack in a slot, alignment of samples in the linear rack at a position accessible by a pipetter of pipetting station, transfer of a linear rack containing control samples into the control storage element 4, etc. The carousels 2 and 3 can be advanced any amount chosen under computer control, and are preferably not simple incrementally advanced devices. Further, as discussed above, the carousels 2 and 3 are preferably advancible in half increments so as to allow components of a linear transfer mechanism to either exit the carousel, or to allow insertion of the component into the carousel (via the grooved underside 28 of wedge region 12) to retrieve a linear rack therefrom. Specifically, with reference to FIG. 3, to retrieve a rack from one carousel and to transfer the rack to either another carousel, a control storage compartment or the rack loader (when ejecting the rack), an upward projection of the transfer mechanism will travel into the carousel through groove 28, then, with a one half incremental advance, the projection will move into a position of engagement under the linear rack, and finally, with a linear movement along track 29, the linear rack will be removed from the carousel.

Figure 4:
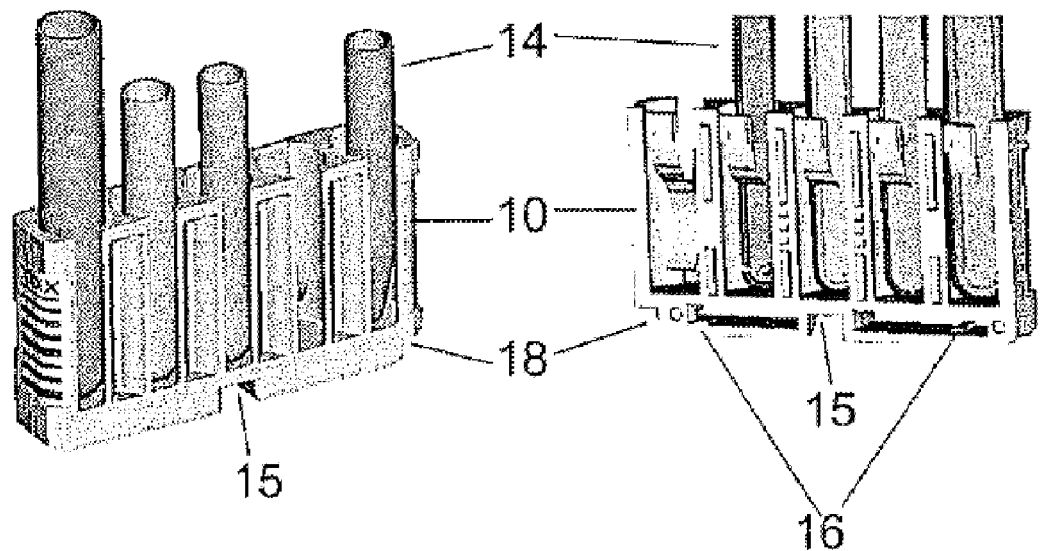
FIGS. 4a and 4b are illustration of a sample rack in a left side view and a cross-sectional view respectively.

FIGS. 4a and 4b show an isometric side view and a cross-sectional side view of the preferred linear racks 10 used in the practice of this invention. In the preferred embodiment, each linear rack 10 will hold a plurality of sample tubes 14 and, while five tubes 14 are shown in the drawings, the number can vary within the practice of the invention. The tubes 14 can be of varying size, and in an automated immunoassay analyzer embodiment contemplated by this invention, the tubes may range in diameter from 11 mm to 16 mm, and may range in height from 66 mm to 100 mm. To enable the accommodation of different sized tubes 14 and to allow for easy insertion into a station in the linear rack, the linear racks 10 may have a spring bias in a back wall of each station of the rack, and the front portion of each station may be open. However, it should be clear that the stations for accommodating the tubes 14 can be fully closed and may not require a spring bias mechanism.

FIGS. 4a and 4b also make clear that the racks 10 do not need to be fully loaded during operation and use. That is, some stations may be empty.

The bar code shown on the end of the rack 10 in FIG. 4a identifies the linear rack 10. As can be seen in FIG. 4a, preferably, the linear rack has a closed back side and an open front side. This will allow bar codes affixed to the tubes 14 to be read simultaneously with the same bar code reader that reads the bar code label on the rack 10. The bar code can be a label which is printed automatically by a computer, or may be generated by a technician when the tubes 14 are loaded into the linear rack 10, with the label being attachable and detachable from the rack 10 and sample tubes 14. However, in some applications, the linear rack 10 may be permanently marked (e.g., racks for control samples, etc.). As noted above, RFID tags might be used on the linear racks 10 and test tubes 14 instead of bar code labels.

FIGS. 4a and 4b also show that the linear racks 10 preferably include a transfer pin slot 15 in its base. As will be described in more detail below, this transfer pin slot 15 is used by one or more transfer mechanisms within the automated chemical or biological analyzer to move the linear racks 10 between stations (e.g., between carousels, between the rack loader and a carousel, between a carousel and a control storage component). Movement of the linear rack 10 may be accomplished, for example, by an upwardly projecting element engaging the pin slot 15, then sliding the rack 10 in a given direction, then having the projecting element disengage from the linear rack 10 (such as by rotational movement of the carousel and withdrawal of the upwardly projecting element through the grooved region 28 in a wedge section 12 of the carousel). It should be understood that other types of features might be incorporated into a linear rack 10 to assist in transfer operations, and that if a transfer pin slot 15 is used, as in the preferred embodiment, the location of the transfer pin slot 15 on the linear rack 10 may vary within the practice of the invention. Further, linear racks 10 might include more than one feature to assist in movement between stations in the automated chemical and biological analyzer (e.g., more than one transfer pin slot 15, etc.).

FIGS. 4a and 4b also show that the linear rack 10 may also be formed with a detent 16 (to be discussed in more detail below) to assist in loading the linear rack 10 into a carousel 2 or 3, and indentation region 18 which may assist in identifying the front end and back of the rack so that a technician does not insert the linear rack 10 in a rack loader incorrectly. It should be understood that the construction of the linear rack can vary considerably within the practice of the invention. The linear configuration allows for easy identification of a plurality of samples located at different spaces along the length of the linear rack 10, easy loading of samples into the rack by technicians, and easy handling of the rack 10 by an automated rack loader. Furthermore, the linear configuration of the racks 10, in conjunction with the carousels 2 or 3 of the present invention, permits the linear rack 10 to be transferred to a plurality of stations within an automated chemical or biological analyzer via simple linear movements of transfer devices (turning of the linear racks 10 is not required).

Figure 5:
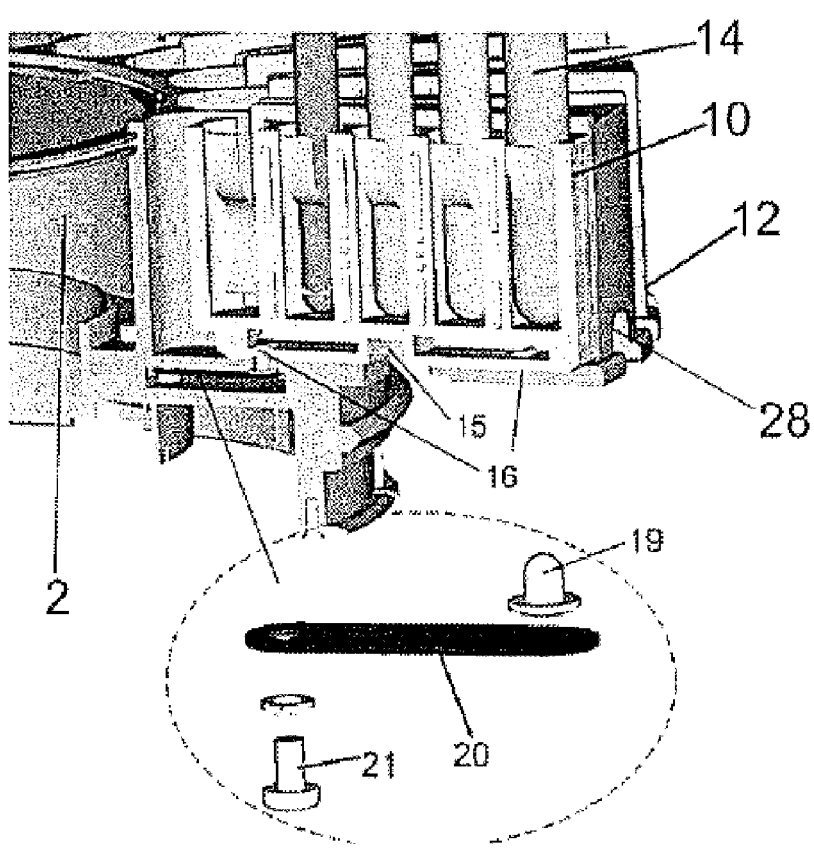
FIG. 5 is an illustration of the rack mounting mechanism.

FIG. 5 highlights a preferred mechanism for retention of a linear rack 10 filled with a plurality of sample tubes 14 in a slot 11 of a carousel 2 (or 3). Specifically, in a preferred embodiment, a button 19 positioned on flat spring 20 secured to the carousel 2 by connector 21 is biased upwards so as to engage detent 16 in the bottom of the linear rack 10. When the linear rack 10 is moved into the slot 11 of the carousel by the transfer mechanism, it is secured in the carousel by the button 19 engaging the detent 16. As explained above, the upwardly projecting member of the transfer mechanism is then permitted to exit the carousel by rotational movement of the carousel 2 such that the upwardly projecting member slides laterally out of engagement with the transfer pin slot 15. Thereafter, the upwardly projecting member is permitted to slide out of the carousel 2 (or 3) through the groove 28 at the bottom of the adjacent wedge portion 12. Similarly, when the linear rack 10 is to be withdrawn from the carousel, the upwardly projecting member engages the transfer pin slot 15 and is used to pull the linear rack 10 out of the slot 11 in the carousel 2 (or 3). During removal, the button 19 is pushed downward by the base of the linear rack 10, thereby allowing the linear rack 10 to be transferred to its destination.

In FIG. 5 it can be seen that the bottom of the linear rack 10 preferably has detents 16 on its base at both ends. These detents 16 would be used, for example, when the linear rack 10 is transferred from one carousel to another (e.g., the first carousel would have a button member for engaging one end of the linear rack and the second carousel would have a button member for engaging the other end of the linear rack 10). It should be understood that other configurations can be employed for temporarily securing the linear rack 10 within a carousel or at another station (e.g., control storage element 4), and that in some applications, a securing feature, such as the button 19/detent 16 combination, may not be required.

Figure 6:
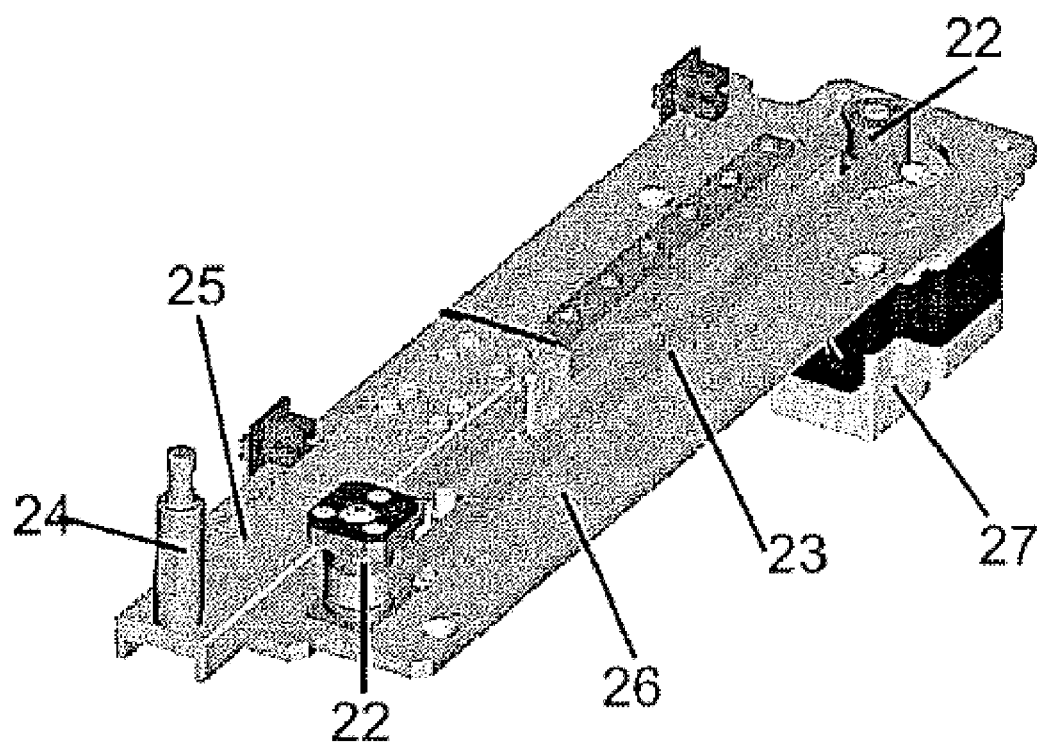
FIG. 6 is an illustration of a transfer mechanism.

FIG. 6 illustrates a preferred transfer mechanism used, for example, to transfer linear racks 10 from an automated rack loader to a carousel, to make transfers between carousels, and to make transfers to a control storage compartment. Preferably, a drive belt 23 or chain positioned on spindles 22 is used to move back and forth a transfer slide 25 having an upwardly projecting transfer pin 24. Movement is achieved under computer control of the motor 27. As discussed above, once the transfer pin 24 is positioned in the transfer slot 15 on the underside of a linear rack 10, the transfer slide 25 and pin 24 are used to transport the linear rack 10 into or out of, for example, a carousel 2 or 3. In the preferred embodiment, for simplicity in operation, it is preferred that the transfer mechanism only move in a forward or reverse direction along a straight line. Thus, movements of the transfer mechanisms and carousels must be coordinated under computer control to allow installation of a rack in a carousel with subsequent movement of the transfer pin 24 out of the carousel through the groove in the bottom of the carousel, and vice versa. It should be understood that other transferring mechanisms might be used within the practice of this invention, and that what is required is a mechanism that can be operated under computer control in a coordinated fashion with other moveable components to effect the transfer of a generally linear rack 10 between stations such as between a rack loader and a carousel, between carousels, and between a carousel and a control station.

Figure 7:
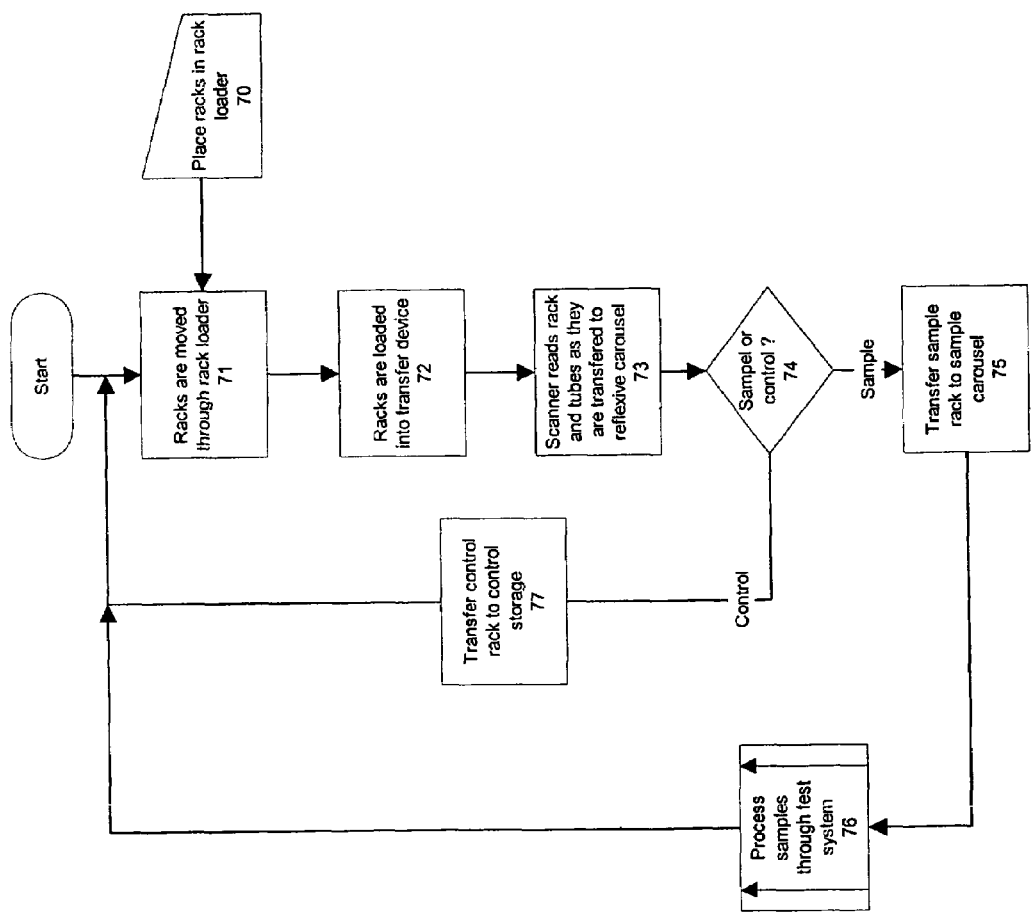
FIG. 7 is a simple flowchart for initiating testing of a sample vessel using the rack and carousel of the invention.

FIG. 7 provides a simple flow diagram which describes a sequence of moving a linear rack 10 in a preferred embodiment of the test instrument (e.g., an automated chemical or biological analyzer) as depicted in FIGS. 1 and 2 of the application. At anytime, sample and control racks can be loaded manually into the rack loader (Step 70). Upon receipt of a start command from the control subsystem 101, the sample racks are moved through the rack loader (Step 71). The racks are then transferred into the "reflexive" carousel 2 by the transfer device 7 at step 72. The sensor 8 reads the identification data from the rack and sample tubes (e.g., bar codes or RFID tags on the rack and sample tubes) and exchanges this data with the control subsystem 101 at step 73. A decision is made at step 74 to determine if the rack that was loaded is a sample rack or a control rack. If the rack is a control rack, the rack is transferred to the control storage 4 at step 77. This is accomplished by movement between one or more carousels, and ultimately installation in a control storage element 4. If the rack is a sample rack, the sample rack is transferred to the sample carousel 3 via the reflexive carousel 2 at step 75. The time when the transfer is made is controlled by subsystem 101, and it should be understood that racks can be moved back and forth between carousels to accommodate different orders in processing samples. Once the sample racks are transferred to the sample carousel, the designated test process can be performed at step 76. In a preferred embodiment of the invention, the computer controller will be programmed to maintain one of the slots in one of the carousels empty (preferably a slot in reflexive carousel 2) so that rush or "STAT" tests can be easily and quickly added to the analyzer for processing at step 71. All of the movements of the carousels and transfer devices, as well as operations of pipetting station 5 are preferably operated under a coordinated, computer control which considers the tests to be performed which have been loaded into the analyzer, as well as any preferences for rush or "STAT" results.

Figure 8:
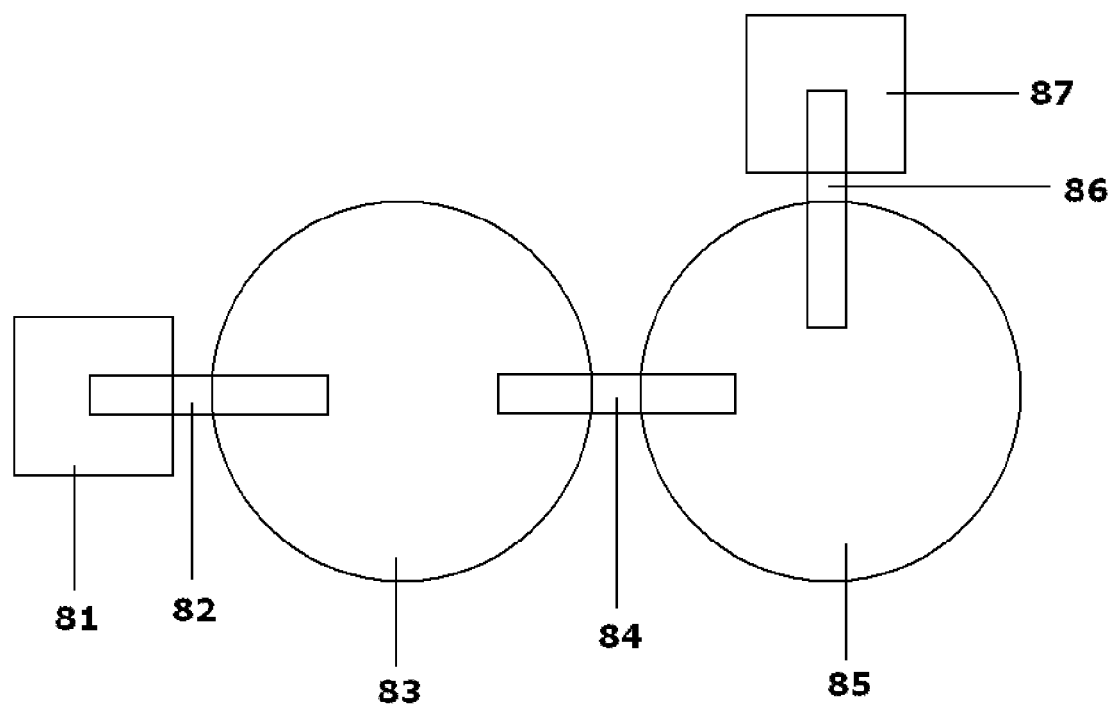
FIG. 8 is a schematic illustration of an automated immunoassay analyzer according to various embodiments of the invention.

FIG. 8 shows a schematic illustration of an automated immunoassay analyzer according to various embodiments of the invention. First transfer device 84 allows for transfer between first carousel 83 and second carousel 85. Second transfer device allows for between first carousel 83 and rack loader 81. Third transfer device allows for transfer between second carousel 85 and control storage component 87.

While the invention has been described in terms of its preferred embodiments, those skilled in the art will recognize that the invention can be practiced with modification within the spirit and scope of the appended claims.

What I claim as new and desire to secure by Letters Patent is as follows:

1. A sample handling system for a chemical or biological material analyzer, comprising:
   a reagent subsystem;
   a sample subsystem including a plurality of non-concentric carousels located on a platform of the analyzer,
      wherein each carousel comprises means for holding a plurality of sample racks, wherein each holding means comprises a plurality of slots distributed radially about a perimeter of the carousel; and a transfer device comprising means for moving a sample rack directly between opposed, radially-aligned slots of two non-concentric carousels and between the perimeter of both of the two non-concentric carousels.

2. The sample handling system of claim 1, wherein the transfer device comprises means for engaging a transfer slot positioned in a base of a sample rack.

3. The sample handling system of claim 2, wherein the engaging means comprises a pin sized to slidably engage the transfer slot.

4. The sample handling system of claim 1, wherein the moving means of the transfer device moves linearly.

5. The sample handling system of claim 4, wherein the moving means comprises, a belt, a plurality of spindles, and a motor, wherein the motor driveably engages a spindle, and the plurality of spindles, partially rotationally engages the belt.

6. The sample handling system of claim 1, wherein the transfer device comprises, a transfer slide for moving a sample rack between aligned slots of the two non-concentric carousels.

7. The sample handling system of claim 1, further comprising a programmable controller programmed to coordinate movements of the transfer device and at least one of the carousels.

8. The sample handling system of claim 7, wherein the programmable controller is programmed to determine an optimized order for processing a plurality of samples, and wherein the determination of the optimized order is based, at least in part, on a processing requirement associated with each of the plurality of samples, and on any rush or STAT requests for any of the samples.

9. The sample handling system of claim 7, wherein the programmable controller is programmed to maintain at least one slot in at least one carousel empty in order to permit priority loading of a sample rack.

10. The sample handling system of claim 1, wherein the carousels are circular in shape.

11. The sample handling system of claim 1, wherein at least two carousels are the same size.

12. The sample handling system of claim 1, wherein at least one carousel is rotatable 360 degrees in both a clockwise and a counter-clockwise direction.

13. The sample handling system of claim 1, wherein each of the plurality of carousels is rotatable 360 degrees in both a clockwise and a counter-clockwise direction.

14. The sample handling system of claim 1, wherein at least one carousel further comprises means for engaging a detent on a base of a sample rack.

15. The sample handling system of claim 14, wherein the engaging means comprises a button member positioned at a base of a slot.

16. The sample handling system of claim 15, wherein the engaging means further comprises a means for biasing the button member towards the sample rack with which the button member engages.

17. The sample handling system of claim 16, wherein the biasing means comprises a flat spring.

18. The sample handling system of claim 1, further comprising means for biasing a sample rack against a side wall of a slot.

19. The sample handling system of claim 18, wherein the biasing means is a spring positioned on a side wall of a slot.

20. The sample handling system of claim 1, further comprising means for reading a label associated with a sample rack, and means for transmitting information from said label to a controller.

21. The sample handling system of claim 20, wherein the reading means comprises a label reader positioned adjacent to the transfer device.

22. The sample handling system of claim 21, wherein the label is a bar code.

23. The sample handling system of claim 21, wherein the label is an RFID tag.

24. A sample handling system of claim 1, further comprising means for identifying the contents of a sample rack.

25. The sample handling system of claim 1, further comprising an automated rack loader and a second transfer device comprising means for moving a sample rack between a carousel and the rack loader.

26. The sample handling system of claim 1, further comprising:
a control storage component positioned adjacent to a carousel, and
a second transfer device comprising means for moving a sample rack between the control storage component and the carousel positioned adjacent to the control storage component.

27. The sample handling system of claim 1, wherein the sample rack comprises means for holding a plurality of samples.

28. The sample handling system of claim 27, wherein the sample rack comprises means for holding at least five samples.

29. The sample handling system of claim 27, wherein the sample rack is linear.

30. A sample handling system for a chemical or biological material analyzer, comprising:
a sample rack configured to hold at least one sample tube containing patient sample or control sample;
a plurality of non-concentric carousels located on a platform, wherein each carousel comprises a plurality of slots distributed radially about a perimeter of the carousel, each of the slots being configured to hold the sample rack; and
a transfer device configured to transport the sample rack directly between opposed, radially-aligned slots of two non-concentric carousels and between the perimeter of both of the two non-concentric carousels.

31. The sample handling system of claim 30, wherein the transfer device comprises a pin sized to slidably engage a transfer slot positioned in a base of the sample rack.

32. The sample handling system of claim 30, further comprising a programmable controller programmed to coordinate movements of the transfer device and at least one of the carousels,
wherein the programmable controller is programmed to determine an optimized order for processing a plurality of samples,
wherein the determination of the optimized order is based, at least in part, on a processing requirement associated with each of the plurality of samples, and on any rush or STAT requests for any of the samples, and
wherein the programmable controller is programmed to maintain at least one slot in at least one carousel empty in order to permit priority loading of the sample rack.

33. The sample handling system of claim 30, further comprising:

a spring positioned on a first side wall of a slot, the spring biasing a sample rack against a second side wall of the slot;

a label reader for reading a label associated with the sample rack, wherein the label reader is positioned adjacent to the transfer device;

an automated rack loader and a second transfer device comprising means for moving the sample rack between a carousel and the rack loader;

a control storage component positioned adjacent to a carousel; and a third transfer device disposing the sample rack between a slot and the control storage component, and wherein at least one carousel further comprises a button member positioned at a base of a slot, and a flat spring, biasing the button member to engage a detent on a base of the sample rack.

34. A sample handling system for a chemical or biological material analyzer, comprising:

a platform;

two non-concentric carousels located on the platform, each of the plurality of non-concentric carousels including slots, the slots extending along a radius of each of the plurality of carousels to a outermost radial perimeter thereof, the slots being adapted to hold a plurality of sample racks, and wherein guide slots are formed in each of the slots; and a transfer mechanism including a projecting element moveable in the guide slots and adapted to engage a sample rack to move the sample rack directly between opposed, radially-aligned slots of the radial perimeters of the two non-concentric carousels.

* * * * *